(12) United States Patent
Faizan et al.

(10) Patent No.: US 12,032,156 B2
(45) Date of Patent: Jul. 9, 2024

(54) APPARATUS TO ENABLE DIFFERENTLY ABLED USERS TO COMMUNICATE AND A METHOD THEREOF

(71) Applicant: Mirza Faizan, Irving, TX (US)

(72) Inventors: Mirza Faizan, Irving, TX (US); Yashas Vamsi Pradeep, Frisco, TX (US); Zayn Sohel Sachak, Coppel, TX (US); Gautam Rao, Irving, TX (US); Hamza Ali Zakir, Irving, TX (US); Sanjiv Sridharan, Irving, TX (US); Sheza Asif, Parker, TX (US); Mishaal Qureshi, Frisco, TX (US); Iliyan Ali Mithani, Allen, TX (US); Vihan Yerubandi, Southlake, TX (US); Nihal Yerubandi, Southlake, TX (US); Abdullah Ali Syed, Wylie, TX (US); Avaneesh Jakkireddy, Allen, TX (US); Raj Kusumakar, Grapevine, TX (US); Abdullah Hasani, Murphy, TX (US)

( * ) Notice: Subject to any disclaimer, the term of this patent is extended or adjusted under 35 U.S.C. 154(b) by 0 days.

(21) Appl. No.: 17/716,637

(22) Filed: Apr. 8, 2022

(65) Prior Publication Data
US 2023/0324680 A1    Oct. 12, 2023

(51) Int. Cl.
| | | |
|---|---|---|
| G02B 27/00 | (2006.01) | |
| G01S 17/88 | (2006.01) | |
| G02B 27/01 | (2006.01) | |
| G06F 3/04817 | (2022.01) | |

(52) U.S. Cl.
CPC .......... *G02B 27/0093* (2013.01); *G01S 17/88* (2013.01); *G02B 27/0172* (2013.01); *G06F 3/04817* (2013.01)

(58) Field of Classification Search
CPC . G02B 27/0093; G02B 27/0172; G01S 17/88; G06F 3/04817
See application file for complete search history.

(56) References Cited

U.S. PATENT DOCUMENTS

| | | | | |
|---|---|---|---|---|
| 4,748,502 | A * | 5/1988 | Friedman | G06T 7/70 348/78 |
| 7,624,355 | B2 * | 11/2009 | Baneth | G06F 3/04886 715/822 |
| 9,612,656 | B2 * | 4/2017 | Sztuk | G06V 40/19 |
| 10,039,445 | B1 * | 8/2018 | Torch | A61B 5/18 |
| 10,372,204 | B2 * | 8/2019 | Tungare | G06F 3/013 |
| 11,612,342 | B2 * | 3/2023 | Kornberg | A61B 5/7267 600/301 |
| 2002/0175897 | A1 * | 11/2002 | Pelosi | G06F 3/012 345/158 |
| 2013/0307771 | A1 * | 11/2013 | Parker | G06F 3/167 345/158 |
| 2016/0195924 | A1 * | 7/2016 | Weber | G06F 3/013 345/156 |
| 2020/0022577 | A1 * | 1/2020 | Rishoni | G06F 3/0236 |
| 2020/0096774 | A1 * | 3/2020 | Trail | G06T 7/70 |

* cited by examiner

*Primary Examiner* — Bryan Earles

(57) ABSTRACT

The present disclosure envisages an apparatus for communication to enable differently abled users to communicate their requirements to others. The apparatus comprises an eye wearable device adapted to emit infrared light signal from a certain area of at least one eye of the user. The apparatus further includes a monitoring device configured to receive the transmitted infrared light signal from the at least one eye of the user and further configured to identify the requirement of the user corresponding to the transmitted infrared light signal.

5 Claims, 2 Drawing Sheets

APPARATUS TO ENABLE DIFFERENTLY ABLED USERS TO COMMUNICATE AND A METHOD THEREOF

FIELD

The present disclosure relates to the field of optical devices. More specifically, the invention belongs to the field of optical devices to enable differently-abled users to communicate their requirements to others.

BACKGROUND

In the present age of advanced technology, physically challenged people should also have ease of life. Physically challenged people find it difficult to express their needs to others. This becomes an obstacle for them in leading a normal healthy life. It is common amongst physically challenged to associate their needs with suitable words and are often misunderstood. This lack of proper communication with others can take a mental toll on such a person. It further may lead to emergencies like medical negligence etc.

Conventionally, the problem is solved by keeping a trained helper along with the physically challenged people. These helpers are often trained to understand the needs of physically challenged people. However, this may not be an accurate solution for physically challenged people, as these translators or helpers may also get confused. The confusion may lead to serious harm and frustrations to physically challenged people. Moreover, this option can turn out expensive and not everyone can afford it.

To solve the aforesaid problem, suitable human-machine interfaces were used. These interfaces are incorporated with verbal command detection techniques. The physically challenged people may provide verbal commands to these interfaces and a corresponding action stored in the repository is activated in response to such commands. Unfortunately, these interfaces are limiting for users that cannot speak or see. These categories of physically challenged people cannot accurately use these interfaces and hence become another challenge for them.

Another domain of technology used for the physically disabled is optical detectors. The optical detector includes a spatial light modulator being adapted to modify at least one optical property of a light beam in a spatially resolved fashion, having a matrix of pixels, each pixel being controllable to individually modify the at least one optical property of a portion of the light beam passing the pixel. An optical sensor is adapted to detect the light beam after passing the matrix of pixels of the spatial light modulator and to generate at least one sensor signal, wherein the at least one optical sensor comprises a stack of at least two optical sensors, wherein at least one of the optical sensors of the stack is a pixelated optical sensor having a plurality of light-sensitive pixels. The modulator device is adapted for periodically controlling at least two of the pixels of the matrix of pixels of the spatial light modulator with different modulation frequencies. An evaluation device adapted for performing a frequency analysis in order to determine signal components of the sensor signal for the modulation frequencies. This technology fails to provide ease of selection of actions and further provides a limited set of pre-determined actions.

There is, therefore, felt a need for an apparatus and method that facilitate tracking of the eye movement of physically challenged people. The present invention provides apparatus and method that is capable of providing predictive text algorithms to make communication faster based on words commonly used together.

Objects

Some of the objects of the present disclosure, which at least one embodiment herein satisfies, are as follows:

An object of the present disclosure is to provide an apparatus and a method that enable differently-abled users to communicate their needs to others.

Another object of the present disclosure is to provide an apparatus and a method that facilitate tracking of the eye movement of physically challenged people.

Still another object of the present disclosure is to provide an apparatus and a method that provide predictive text algorithms to make communication faster based on words commonly used together.

Yet another object of the present disclosure is to provide an apparatus and a method that provide a portable screen that can be mounted to a variety of surfaces.

A further object of the present disclosure is to provide an apparatus and a method that transmits infrared light from the area of the user's eye.

A still further object of the present disclosure is to provide an apparatus and a method that use glasses or lenses or both and provide easy charging.

An object of the present disclosure is to provide an apparatus and a method that use glasses or lenses or both and provide easy charging.

Other objects and advantages of the present disclosure will be more apparent from the following description, which is not intended to limit the scope of the present disclosure.

SUMMARY

The present invention envisages an apparatus and a method to enable differently-abled users to communicate their requirements to others. The apparatus comprises an eye wearable device adapted to emit an infrared light signal from a certain area of at least one eye of the user and a monitoring device connected to the eye wearable device through a communication network.

The monitoring device is configured to receive the transmitted infrared light signal from at least one eye of the user and further configured to identify the requirement of the user corresponding to the transmitted infrared light signal.

In an embodiment, the monitoring device comprises a receiving module configured to receive the transmitted infrared light signal from at least one eye of the user.

The monitoring device further comprises a determination module configured to determine a point of gaze of the differently-abled user corresponding to the transmitted infrared light signal.

The monitoring device further includes an identification module configured to identify the requirement of the user based on determining point of gaze and an output module configured to provide an audio output corresponding to the identified icon of the cell of the matrix presented on the optical screen.

In an embodiment, receiving module includes a plurality of icons arranged in a matrix, wherein each icon corresponds to a cell in the matrix.

In another embodiment, each cell includes at least one infra-red sensor configured to capture the point of gaze.

In still another embodiment, at least one infra-red sensor is a LIDAR sensor.

In yet another embodiment, the eye wearable device includes at least one of a lens and a glass.

In a further embodiment, the eye wearable device is charged via an induction device.

In a still further embodiment, the monitoring device is further configured to operate in at least one of a predictive word generation mode and a preset phase mode by employing at least one of the machine learning techniques.

In an embodiment, the predictive word generation mode is configured to predict the requirement based on the movement of the eyes of the user; and the preset phase mode is configured to generate pre-defined phrases based on a usage frequency of the requirement.

A method for communication to enable differently-abled users to communicate their requirements, the method comprising steps of:
transmitting an infrared light signal from a certain area of at least one eye of the user and transmitting the same;
receiving the transmitted infrared light signal from at least one eye of the user;
determining a point of gaze of the differently-abled user corresponding to the transmitted infrared light signal;
identifying the requirement of the user based on determined the point of gaze; and
providing an audio output corresponding to the identified requirement.

These and other features, advantages, and objects of the various embodiments will be better understood with reference to the following drawings, specifications and claims.

BRIEF DESCRIPTION OF THE ACCOMPANYING DRAWING

The accompanying drawings, which are included to provide a further understanding of the invention and are incorporated in and constitute a part of this specification, illustrate embodiments of the invention and together with the description serve to explain the principles of the invention.

Further, the accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears.

The same numbers are used throughout the figures to reference like features and components. Some embodiments of system and/or methods in accordance with embodiments of the present subject matter are now described, by way of example only, and with reference to the accompanying figures, in which:

Features, elements, and aspects of the invention that are referenced by the same numerals in different figures represent the same, equivalent, or similar features, elements, or aspects in accordance with one or more embodiments.

The following figure depicts certain illustrative embodiment of the invention. This depicted embodiment is to be understood as illustrative of the invention and not as limiting in any way.

Referring particularly to the drawing for the purpose of illustration only and not limitation, there is illustrated:

An apparatus for communication to enable differently abled users to communicate their requirements to others, is now described in accordance with preferred embodiment of the present disclosure, in which.

LIST OF REFERENCE NUMERALS

Figure 1:
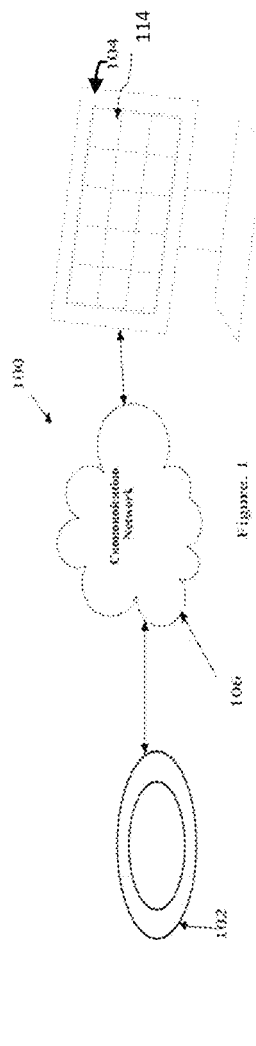
FIG. 1 illustrates an exemplary network environment of an apparatus for communication to enable differently-abled users to communicate their requirements to others, in accordance with an embodiment of the present disclosure.

100— Apparatus
102— Eye wearable device
104— Monitoring device
106— Communication network
108— Memory
110— Processor
112— Interface
202— Receiving module
204— Determination module
206— Identification module
208— Output module
210— Configuration data
212— Device and application data
214— User related data
216— Other data

DETAILED DESCRIPTION

Embodiments, of the present disclosure, will now be described with reference to the accompanying drawing.

In said drawings, numeral 100 denotes an apparatus for communication to enable differently-abled users to communicate their requirements to others, according to the invention as a whole.

Embodiments are provided so as to thoroughly and fully convey the scope of the present disclosure to the person skilled in the art. Numerous details are set forth relating to specific components, and methods, to provide a complete understanding of embodiments of the present disclosure. It will be apparent to the person skilled in the art that the details provided in the embodiments should not be construed to limit the scope of the present disclosure.

In some embodiments, well-known processes, well-known apparatus structures, and well-known techniques are not described in detail.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

The following detailed description illustrates the invention by way of example, and not by way of limitation. This description will clearly enable one skilled in the art to make and use the invention and describes several embodiments, adaptions, variations, alternatives, and uses of the invention, including what we presently believe is the best mode of carrying out the invention.

The present invention envisages an apparatus and method that facilitate tracking of the eye movement of physically challenged people. The present invention provides apparatus and method that is capable of providing predictive text algorithms to make communication faster based on words commonly used together.

The present invention will now be described with reference to FIG. 1 of the preferred embodiment of the present invention. The present invention discloses an apparatus 100 for communication to enable differently-abled users to communicate their requirements to others. The apparatus 100 specifically includes an eye wearable device 102 and a monitoring device 104.

The apparatus 100 is not limited to only components 102 and 104 as communication between 102 and 104 is provided by device of the communication network 106. Network connectivity can be wired or wireless between 102 and 104. However, wireless connectivity is preferable for the convenience of the user. Examples of wireless connectivity between 102 and 104 can be selected from Bluetooth, infrared and other types that support devices in proximity to connect.

In an embodiment, the communication network 106 may include, but is not limited to, a direct interconnection, an e-commerce network, a Peer-to-Peer (P2P) network, Local Area Network (LAN), Wide Area Network (WAN), wireless network (for example, using Wireless Application Protocol), Internet, Wi-Fi and the like.

The eye wearable device 102 is adapted to emit an infrared light signal from a certain area of at least one eye of said user. In an embodiment, the eye wearable device can either be a lens or a glass. In either case, the eye wearable device 102 requires charging that is preferably accomplished by an induction device.

In a preferred embodiment, the lenses discussed here are contact lenses that contain infrared LEDs or vessel units. These infrared LEDs or vessel units facilitate the emission of infrared light from the area of the user's eye.

In another preferred embodiment, the user may choose glasses that are simple in design, i.e., a frame or could be made according to the user's prescription. The glasses contain inductive coils in the front frame and batteries in the side handles for charging purposes.

Considering the above-said embodiments, the user wears the infrared embedded contact lenses. The user wears the glasses to power the IR LEDs in the contact lenses via induction.

In a preferred embodiment, an electromagnetic coil is used for the induction effect. The coil in a charging base creates a magnetic field and is basically an antenna to transmit a field of energy. A second smaller coil in the contact lens receives and harvests the energy and its circuitry converts it back to usable energy for the infrared LEDs.

The apparatus further includes the monitoring device 104 which is configured to receive the transmitted infrared light signal from at least one eye of the user. The monitoring device 104 is further configured to identify the requirement of the user corresponding to the transmitted infrared light signal. p In a working embodiment, assume that the user wants to communicate the command for having 'a glass full of water' on cell 1:1 (1st cell of 1st column). When a user needs a glass of water, he will look at cell 1:1. The IR from his contact lens is transmitted and detected by the IR detector in cell 1:1. The optical screen 114 detects it and waits for user confirmation (usually) and then communicates it to the monitoring device 104 that loudly speaks it. The attendant nearby performs the verbally communicated action.

Figure 2:
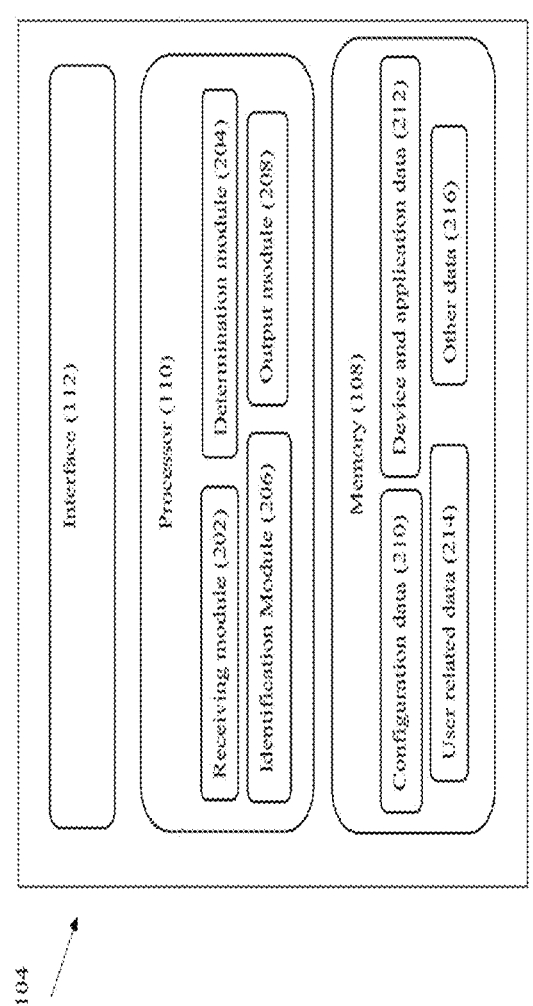
FIG. 2 illustrates an exemplary block diagram of the monitoring device of FIG. 1.

FIG. 2 will now be described with respect to the monitoring device 104 as per the preferred embodiment of the present invention.

In a working embodiment, the monitoring device 104 includes a receiving module 202 configured to receive the transmitted infrared light signal from said at least one eye of the user.

For example, the receiving module 202 can be an optical screen such as the optical screen 114 as shown in FIG. 1. The optical screen 114 can be mounted onto a plethora of surfaces, including a bed, wheelchair, or table via a universal clamp and stand. The screen is also adjustable to the user's preference. For example, completely moving the screen out of the focal point of the user's field of according to the user's posture.

The monitoring device 104 further comprises a determination module 204 configured to determine a point of gaze of the differently-abled user corresponding to the transmitted infrared light signal.

The monitoring device 104 further includes an identification module 206 configured to identify the requirement of the user based on a determined point of gaze.

The monitoring device 104 includes an output module 208 configured to provide an audio output corresponding to the identified icon of the cell of the matrix presented on the optical screen 114.

The receiving module 202 includes a plurality of icons. These icons are arranged in a matrix, wherein each icon corresponds to a cell in the matrix. Further, at least one infra-red sensor is placed on each of the cells that captures the point of gaze.

In an embodiment, the infra-red sensor is a LIDAR sensor.

For example, when a user is willing to communicate with others, he just looks at the receiving module 202 in any of the cells present on the matrix. The IR is transmitted from his contact lens and captured by a particular cell of the matrix. Each cell corresponds to the icon. The moment IR is detected by monitoring device 104, the output module 208 provides a verbal command based on the selected icon.

The functions of the monitoring mean 104 is implemented by a processor 110 that may be a general-purpose processor, a digital signal processor, an application-specific integrated circuit, a field-programmable gate array or another programmable logic device, a discrete gate or transistor logic device, or a discrete hardware component, and can implement or perform the methods, steps, and logical block diagrams disclosed in the embodiments of this invention.

The general-purpose processor may be a microprocessor or any conventional processor or the like. The steps of the method disclosed with reference to the embodiments of this application may be directly performed by a hardware processor or may be performed by using a combination of hardware in the processor and a software unit.

The monitoring device 104 is configured to operate in at least one of a predictive word generation mode and a preset phase mode.

In an embodiment, the predictive word generation mode is configured to predict the requirement based on the movement of the eyes of the user.

In another embodiment, the preset phase mode is configured to generate pre-defined phrases based on the usage frequency of the requirement.

The matrix sets icons for a predictive word generation mode or a preset phase mode based on the selection of the user's preference.

The different modes can be changed easily depending on the needs of the patient and are selected by providing a voice command to an additional voice input device provided on the optical screen.

In the predictive word generation mode, a combination of eye-tracking technology and a predictive word generation algorithm is used. In a working embodiment, a QWERTY keyboard is arranged on the optical screen and an IR sensor is placed on each alphabet. In such a scenario, a combination of eye-tracking technology, a QWERTY keyboard, and a predictive word generation algorithm is used.

In an embodiment, the monitoring device 104 is further configured to operate in at least one of a predictive word generation mode and a preset phase mode by employing at least one of the machine learning techniques.

The predictive word generation mode is configured to predict the requirement based on the movement of said eyes of said user and the preset phase mode is configured to generate pre-defined phrases based on a usage frequency of the requirement.

In another embodiment, the machine learning techniques are selected from the group consisting of predictive analysis techniques and time series analysis techniques.

In yet another embodiment, the machine learning algorithms employed include, but are not limited to, Naïve Bayes, decision trees, linear regression, neural networks, random forest, and the like.

In the preset phase mode, the matrix full of phrases is displayed on the optical screen. As patients tend to use a selected number of phrases quite often in their day-to-day life the first mode might be a less preferred mode. This second mode would provide the user the ability to completely customize the keyboard to contain preset phrases.

Some common examples of such phrases would be "I'm hungry", "Can you open the door?", and others.

This mode would increase convenience and speed up the process of communication. Within this mode, users would also be able to customize many more things about the keyboard, such as font size, pictures associated with the phrases, and even the size of the user interface.

The monitoring device 104 includes Interface or I/O interface 112, a memory 108, and the processor 110. The I/O interface 112 may be configured to receive data from the eye wearable device 102.

The data from the I/O interface 112 may be stored in memory 108. The memory 108 may be communicatively coupled to the processor 110 that executes all the modules.

The memory 108 may also store processor instructions which may cause the processor 110 to execute the instructions for managing continuous execution of the modules.

Further, memory 108 includes various system-related data which are described herein in detail. In an embodiment, data may be stored within the memory 108. The data may include, for example, configuration data 210, device and application data 212, user-related data 214, and other data 216.

The configuration data 210 may include configuration information associated with the monitoring device 104. The configuration data 210 may contain a list of registered users and user devices. In an embodiment, the list is updated when a new user device is registered.

The device and application data may include device configuration information such as device identification number, device type, and supported application identification number, used application details such as, comprises application identifier application type, application state, and application restriction.

The user-related data 214 may include registered user information such as user identification number, date, time, a location associated with the devices.

The other data 216 may store data, including temporary data and temporary files, generated by modules for performing the various functions of the monitoring device 104.

In a nutshell, the apparatus envisaged will create a point of reference to track the user's eye in all lighting conditions. Then an image recognition technique is employed using 'tensor flow' etc. to equate the location of the IR light in the IR camera's line of sight to what the user is looking at on the main display to make a selection for communication. The camera will be able to differentiate infrared light from the contact lenses because it will have infrared pass-through filters fitted in front of them, ensuring that only infrared light passes through to the IR camera.

As mentioned before, image recognition is used for equating what the IR camera is seeing with what the user is trying to select on the screen, will also be inclusive of predictive speech technology so that the computer tries to figure out what the user is trying to communicate, an alphanumeric keyboard screen, image to speech options, and options for preset phrases (user can preset commonly used phrases). When the IR camera sees that the user is looking up, it will see that the IR lights have moved up on the Y-axis, vice versa for looking down.

When the user is looking left or right, the camera and computer will have to interpret the direction of the movement of the IR light dots (IR light dots=what the camera sees) as a mirrored image, since the IR camera is facing the user therefore X-axis movement will have to be mirrored before inputting a selection.

Figure 3:
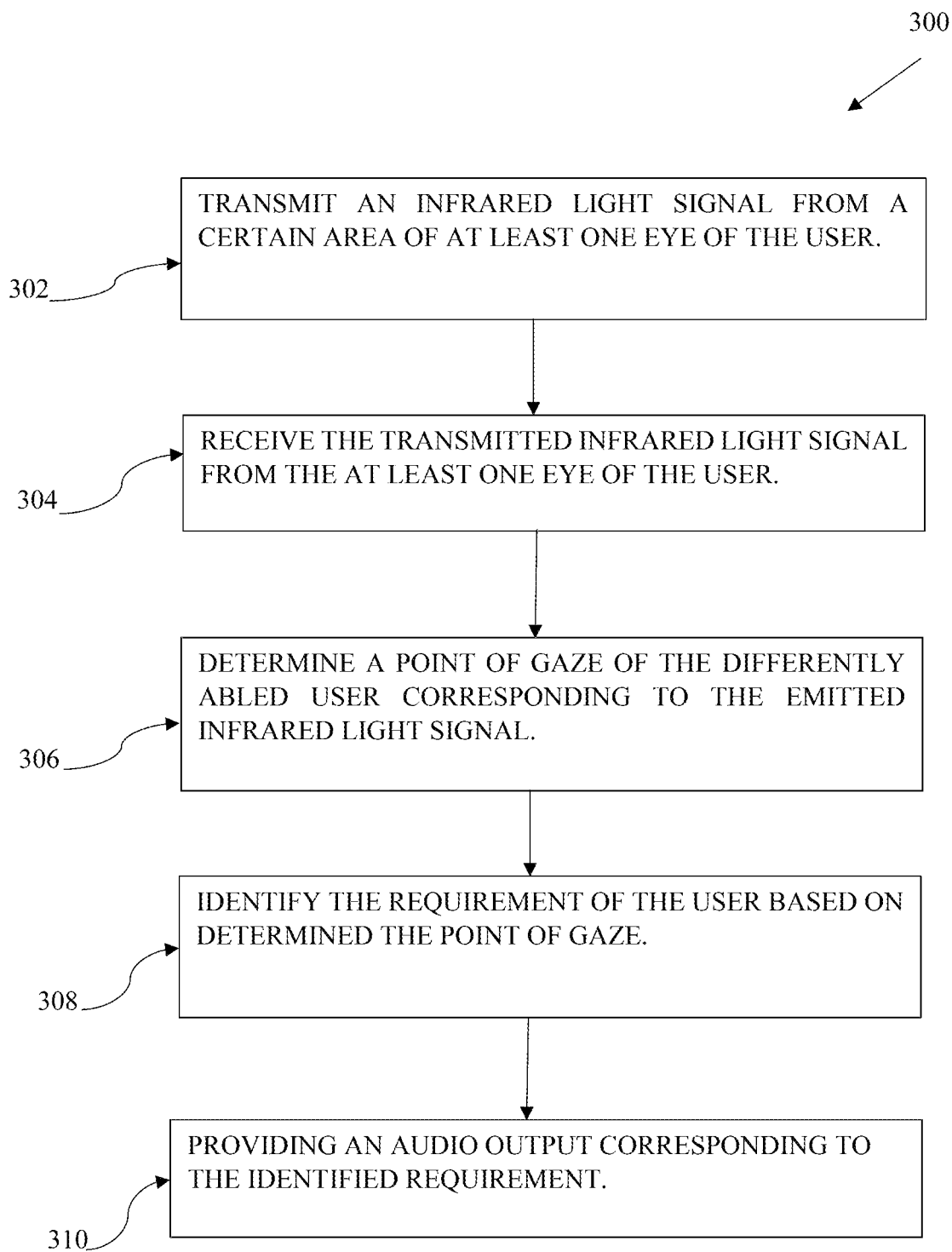
FIG. 3 illustrates a method flow diagram for communication to enable differently-abled users to communicate their requirements to others, in accordance with an embodiment of the present disclosure.

FIG. 3 will now be described that illustrates a method 300 for communication to enable differently-abled users to communicate their requirements.

Method 300 comprises the steps of transmitting (302) an infrared light signal from a certain area of at least one eye of the user and transmitting the same to a monitoring device 104.

The monitoring device receives (304) the transmitted infrared light signal from at least one eye of the user.

The method further comprises determining (306) a point of gaze of the differently-abled user corresponding to the transmitted infrared light signal.

The method further comprises identifying (308) the requirement of the user based on determined the point of gaze and providing (310) an audio output corresponding to the identified requirement.

The transmitted infrared light signal is used for identifying the requirement through a plurality of icons arranged in a matrix. Each icon corresponds to a cell in the matrix.

Therefore, in regards to eye-tracking technology, rather than using a standard infrared eye-tracking solution, a much more accurate method of eye-tracking is envisaged using Lidar. This eye-tracking method works by having the user wear non-prescription contact lenses in order for the Lidar sensor to pick up a difference in depth between the user's iris and sclera and interpret movement.

Additionally, this eye-tracking method is much more efficient and usable than existing infrared trackers because Lidar is not reliant on light, or well-lit environments to supplement imaging.

The user would employ the use of communication boards in order to allow people suffering from paralysis to communicate in a clearer, simpler, and more efficient manner.

The foregoing description of the embodiments has been provided for purposes of illustration and not intended to limit the scope of the present disclosure. Individual components of a particular embodiment are generally not limited to that particular embodiment but are interchangeable. Such variations are not to be regarded as a departure from the present disclosure, and all such modifications are considered to be within the scope of the present disclosure.

Technical Advancements

The present disclosure described hereinabove has several technical advantages including, but not limited to, the realization of an apparatus for communication:
  that enables differently-abled users to communicate their requirements to others;
  that facilitates tracking of the eye movement of physically challenged people
  that provides predictive text algorithms;
  that makes communication faster based on words commonly used together;
  that provides a portable screen which can be mounted to a variety of surfaces;
  that transmits infrared light from the area of the user's eye;
  that uses glasses or lenses or both;
  that provides easy charging device;
  that has simple construction; and
  that is cost-effective.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The use of the expression "at least" or "at least one" suggests the use of one or more elements or ingredients or quantities, as the use may be in the embodiment of the disclosure to achieve one or more of the desired objects or results.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

Therefore, while the embodiments herein have been described in terms of preferred embodiments, those skilled in the art will recognize that the embodiments herein can be practiced with modification within the spirit and scope of the embodiments as described herein.

To the preferred embodiments of the mucus extractor according to the invention, a skilled person, to satisfy contingent requirements, may make modifications, adaptations, and replacements of elements with others functionally equivalent, without departing from the scope of the following claims. Each of the characteristics described as belonging to a possible preferred embodiment can be achieved independently from the other preferred embodiments described.

The above description is considered that of the preferred embodiment(s) only. Modifications of these embodiments will occur to those skilled in the art and to those who make or use the illustrated embodiments. Therefore, it is understood that the embodiment(s) described above are merely exemplary and not intended to limit the scope of this disclosure, which is defined by the following claims as interpreted according to the principles of patent law, including the doctrine of equivalents.

What is claimed is:

1. A system for converting visual commands into audio messages, comprising:
  an IR emitter mounted on a wearable glass, a headband, or a contact lens worn by a user, wherein the IR emitter is configured to emit IR rays in a direction of gaze of the user:
  an add-on portable screen adapted to be externally attached to a device screen, wherein
    the add-on portable screen comprises an infrared (IR) detection module,
    the IR detection module comprises a plurality of cells arranged in matrix form,
    each cell of the plurality of cells includes at least one IR sensor,
    each cell on the add-on portable screen corresponds to a respective icon of a plurality of icons displayed on the device screen, and
    the IR detection module is configured to detect a cell from the plurality of cells on the add-on portable screen which receives the IR rays emitted from the IR emitter; and
  a processor configured to:
    corresponding to the detected cell on the add-on portable screen, determine an icon among the plurality of icons displayed on the device screen;
    map a command identified by the user based on the determined icon on the device screen; and
    play an audio message corresponding to the mapped command.

2. The system of claim 1, wherein the add-on portable screen is attachable to a variety of surfaces.

3. The system of claim 1, wherein the processor is further configured to establish a correspondence between points on the device screen and predefined commands.

4. The system of claim 1, wherein the audio message played by the processor are customizable, allowing users to associate specific commands with personalized audio messages.

5. The system of claim 1, wherein the IR detection module on the add-on portable screen is equipped with a filtering mechanism to minimize interference from ambient IR sources.

* * * * *